US008268007B2

(12) United States Patent
Barsoum et al.

(10) Patent No.: US 8,268,007 B2
(45) Date of Patent: Sep. 18, 2012

(54) MULTI-PIECE PROSTHETIC JOINT COMPONENT

(75) Inventors: Wael K. Barsoum, Bay Village, OH (US); Viktor E. Krebs, Rocky River, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 273 days.

(21) Appl. No.: 12/823,765

(22) Filed: Jun. 25, 2010

(65) Prior Publication Data

US 2010/0331989 A1 Dec. 30, 2010

Related U.S. Application Data

(60) Provisional application No. 61/220,609, filed on Jun. 26, 2009.

(51) Int. Cl.
*A61F 2/30* (2006.01)
(52) U.S. Cl. ............... 623/23.46; 623/21.15; 623/22.42
(58) Field of Classification Search ...... 623/22.4–22.46, 623/23.44–23.46, 21.15–21.17; *A61F 2/30*
See application file for complete search history.

(56) References Cited

U.S. PATENT DOCUMENTS

| | | | |
|---|---|---|---|
| 3,916,451 A | 11/1975 | Buechel et al. | |
| 3,978,528 A | 9/1976 | Crep | |
| 4,279,041 A | 7/1981 | Buchholz | |
| 4,301,553 A | 11/1981 | Noiles | |
| 4,304,011 A | 12/1981 | Whelan, III | |
| 4,352,212 A | 10/1982 | Greene et al. | |
| 4,919,669 A | 4/1990 | Lannelongue | |
| 5,197,989 A | 3/1993 | Hinckfuss et al. | |
| 5,405,400 A | 4/1995 | Linscheid et al. | |
| 5,462,563 A | 10/1995 | Shearer et al. | |
| 5,674,297 A | 10/1997 | Lane et al. | |
| 6,755,866 B2 | 6/2004 | Southworth | |

FOREIGN PATENT DOCUMENTS

| | | |
|---|---|---|
| WO | WO-91/03992 A1 | 4/1991 |
| WO | WO-94/07438 A1 | 4/1994 |

*Primary Examiner* — Thomas J Sweet
*Assistant Examiner* — Jason-Dennis Stewart
(74) *Attorney, Agent, or Firm* — Tarolli, Sundheim, Covell & Tummino LLP

(57) ABSTRACT

An elongate, longitudinally oriented outer sleeve includes an outer sleeve surface defining a radially oriented proximal sleeve border, a radially oriented proximal sleeve rim intersecting the outer sleeve surface at the proximal sleeve border, an outer sleeve body enclosed by the outer sleeve surface and the proximal sleeve rim, and an elongate, longitudinally oriented stem-receiving cavity formed in the outer sleeve body and intersecting the proximal sleeve rim to define a stem-receiving aperture. A joint articulating member includes an elongate, longitudinally oriented stem, an articulating surface, and an interface rim. When the stem is at least partially inserted into the stem-receiving cavity, the proximal sleeve rim and the interface rim interact to change a longitudinal relationship between the outer sleeve and the joint articulating member responsive to relative radially-oriented rotation between the stem and the stem-receiving cavity.

20 Claims, 9 Drawing Sheets

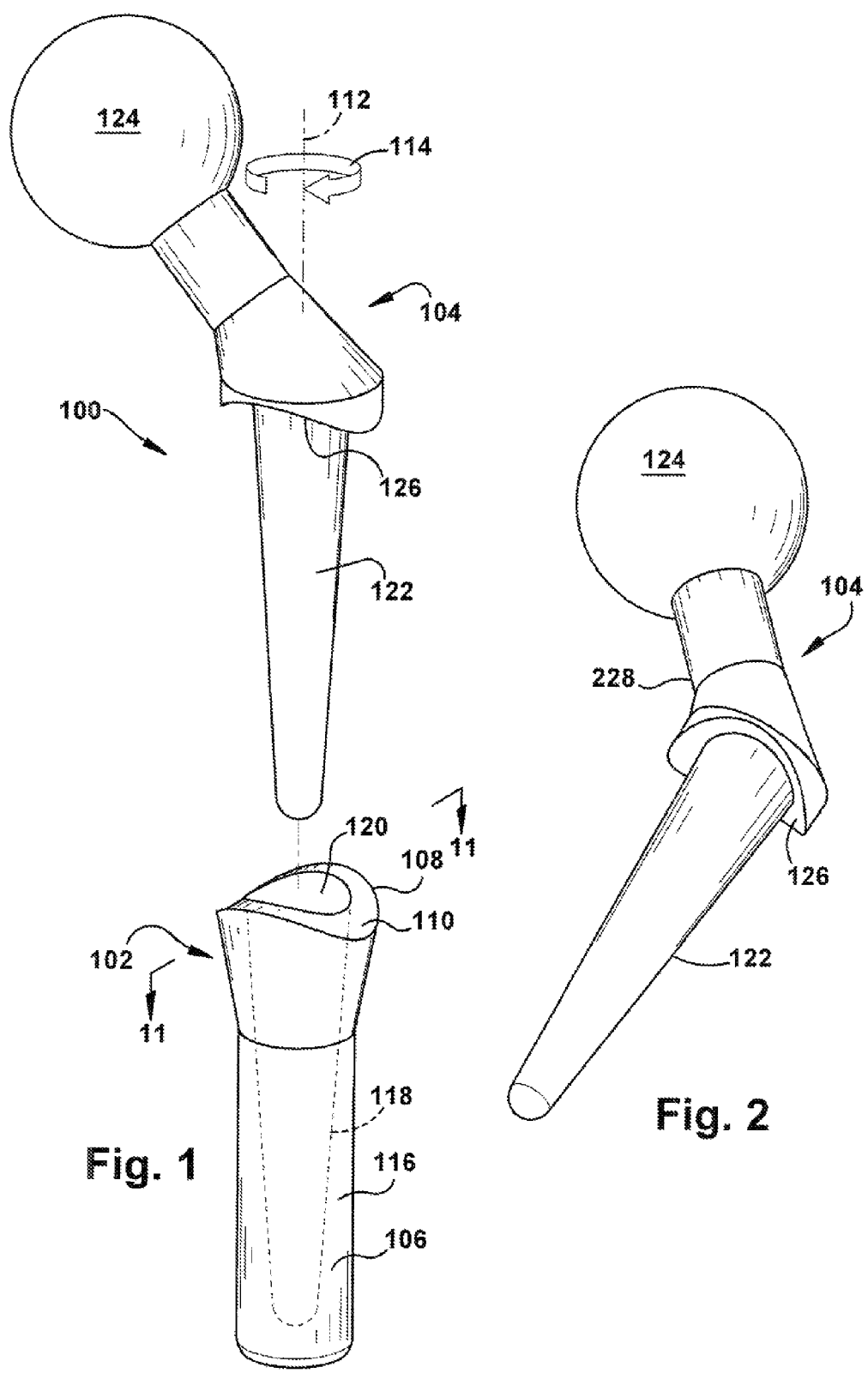

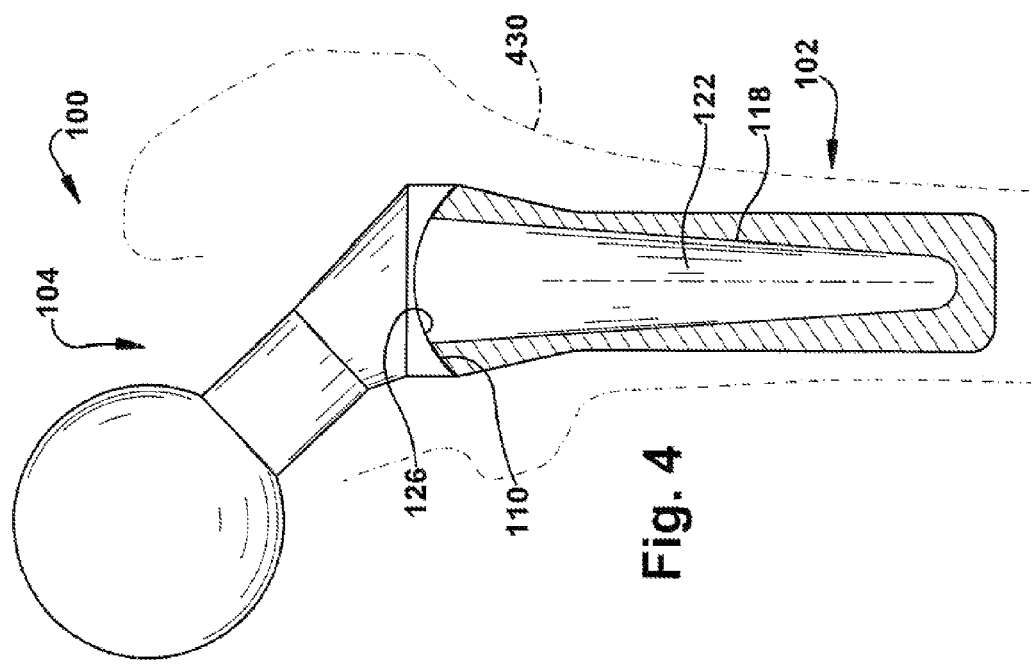
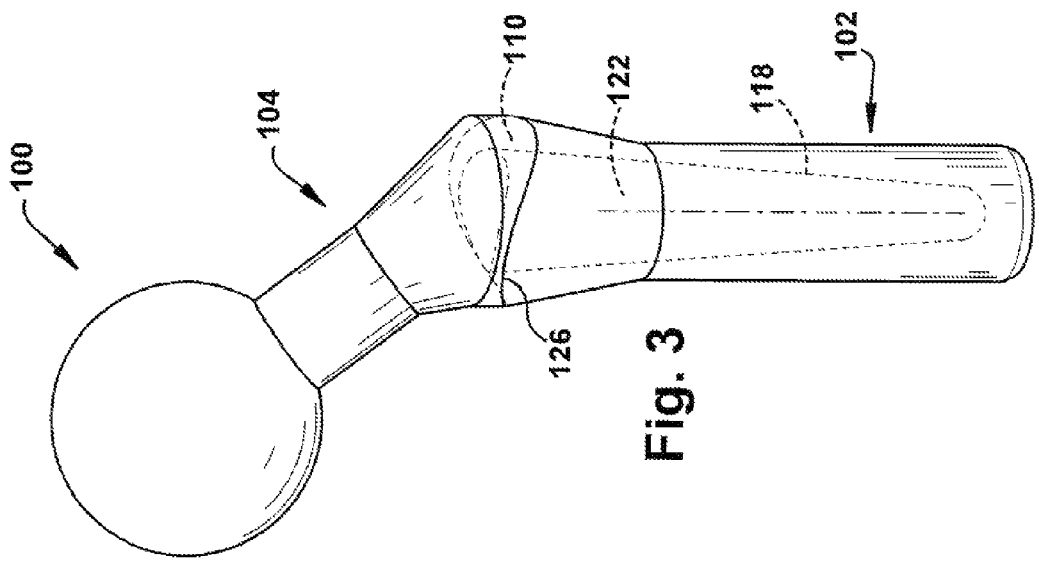

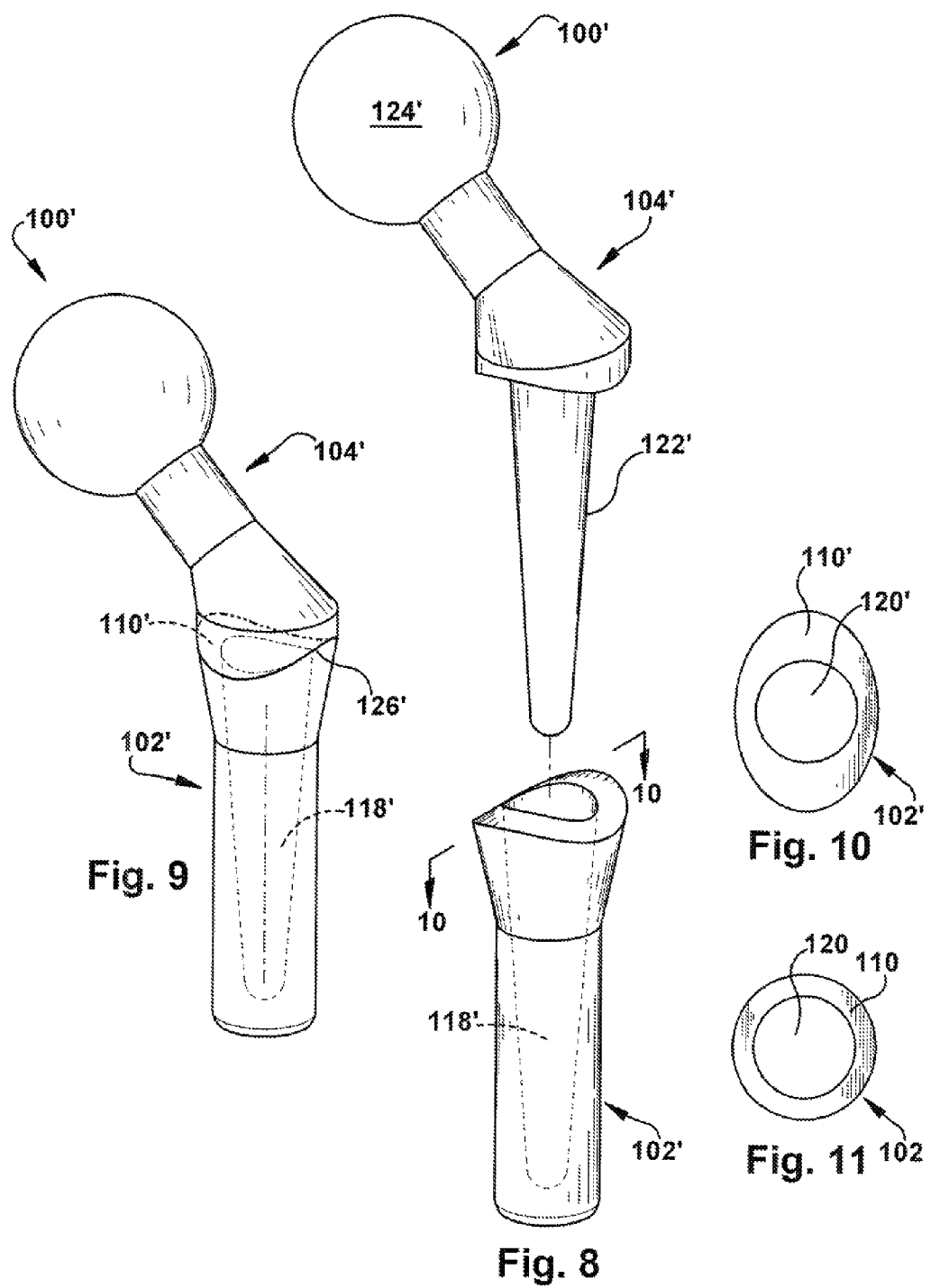

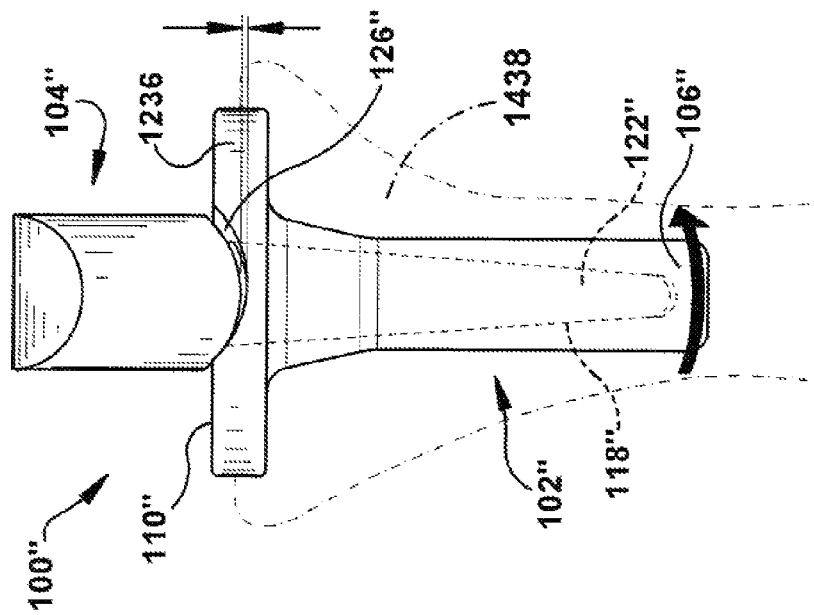
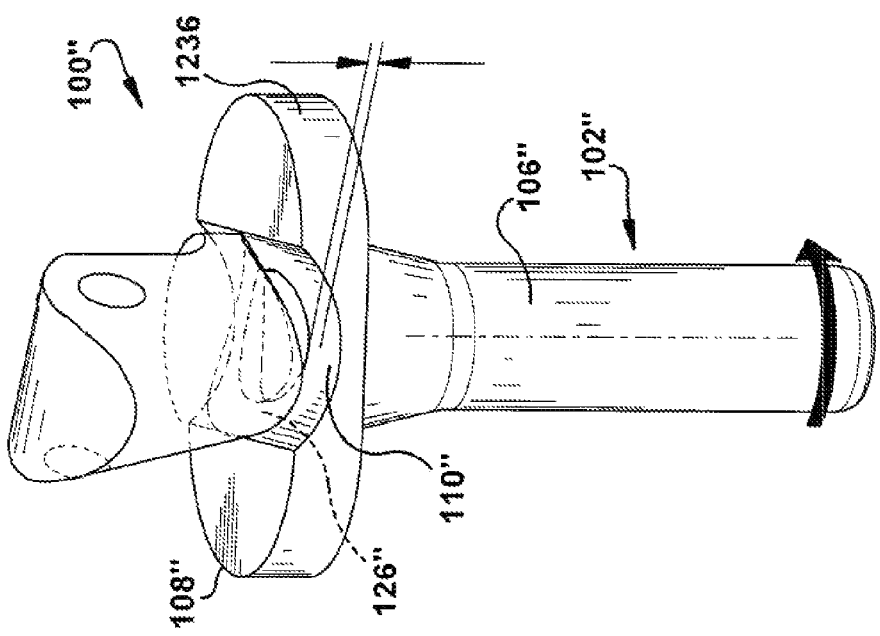

MULTI-PIECE PROSTHETIC JOINT COMPONENT

RELATED APPLICATION

This application claims priority from U.S. Provisional Application No. 61/220,609, filed. Jun. 26, 2009, the subject matter of which is incorporated herein by reference.

TECHNICAL FIELD

The present invention relates to an apparatus and method for use of a multi-piece prosthetic joint component and, more particularly, to a multi-piece prosthetic joint component configured for selective longitudinal expansion.

BACKGROUND OF THE INVENTION

It is known that permanent reconstruction of a bone joint which has been malformed from birth, or as a result of disease, or accidental injury, may be achieved by the substitution of the afflicted portion(s) of the joint by an artificial implant constructed of a biocompatible material. It is desirable that any replacement joint should imitate the natural articulation of the healthy joint.

One method of replacing the hip joint involves the use of a stemmed femoral prosthesis adapted to be inserted and retained within the medullary canal of the femur after removal of the natural femoral head. The socket function of the replacement joint is performed by an acetabular cup implant which defines a spherical recess adapted to receive the ball end of the femoral prosthesis. Dislocation of the femoral ball is prevented by the soft tissue structures and the natural stability of the spherical recess. However, it is possible for the femoral head to be removed from the acetabulum, thus causing a dislocation, for various reasons, including impingement, soft tissue laxity, or component malposition.

Most known hip prostheses require both the femoral and acetabular components to be fixed rigidly into their corresponding bones, either by a tight press-fit, cemented, or screw attachment. Without the ability to rotate the femur completely around its longitudinal axis, due to muscle configuration and surrounding tissue, impingement of known types of hip prostheses is easily possible. Known hip implants include range-of-motion regions posing the danger of aggressive dislocation (by leverage) or implant damage if the femur were to forced violently into such an orientation.

SUMMARY OF THE INVENTION

In an embodiment of the present invention, a multi-piece prosthetic joint component is described. An elongate, longitudinally oriented outer sleeve includes an outer sleeve surface adapted for contact with native bone and defining a radially oriented proximal sleeve border, a radially oriented proximal sleeve rim intersecting the outer sleeve surface at the proximal sleeve border, an outer sleeve body enclosed by the outer sleeve surface and the proximal sleeve rim, and an elongate, longitudinally oriented stem-receiving cavity formed in the outer sleeve body and intersecting the proximal sleeve rim to define a stem-receiving aperture. A joint articulating member includes an elongate, longitudinally oriented stem, an articulating surface, and an interface rim. The stem is longitudinally spaced from the articulating surface and is configured for selective insertion into the stem-receiving cavity. The interface rim is located on the joint articulating member intermediate the stem and the articulating surface. When the stem is at least partially inserted into the stem-receiving cavity, the proximal sleeve rim and the interface rim interact to change a longitudinal relationship between the outer sleeve and the joint articulating member responsive to relative radially-oriented rotation between the stem and the stem-receiving cavity.

In an embodiment of the present invention, a method of providing longitudinal variance to a multi-piece prosthetic joint component is described. An elongate, longitudinally oriented outer sleeve including an outer sleeve surface adapted for contact with native bone and defining a radially oriented proximal sleeve border, a radially oriented proximal sleeve rim intersecting the outer sleeve surface at the proximal sleeve border, an outer sleeve body enclosed by the outer sleeve surface and the proximal sleeve rim, and an elongate, longitudinally oriented stem-receiving cavity formed in the outer sleeve body and intersecting the proximal sleeve rim to define a stem-receiving aperture is provided. A joint articulating member including an elongate, longitudinally oriented stem, an articulating surface, and an interface rim, the stem being longitudinally spaced from the articulating surface and configured for selective insertion into the stem-receiving cavity, and the interface rim being located on the joint articulating member intermediate the stem and the articulating surface is provided. At least a portion of the stem is inserted into the stem-receiving cavity. The stem and the stem-receiving cavity are relatively rotated in a radial orientation. The proximal sleeve rim and the interface rim interact responsive to the relative rotation between the stem and the stem-receiving cavity to change the longitudinal relationship therebetween and accordingly provide longitudinal variance to the multi-piece prosthetic joint component.

BRIEF DESCRIPTION OF THE DRAWINGS

For a better understanding of the invention, reference may be made to the accompanying drawings, in which:

FIG. 1 is an exploded perspective view of an embodiment of the present invention;

FIG. 2 is a partial perspective view of the embodiment of FIG. 1;

FIG. 3 is an assembled view of the embodiment of FIG. 1 in a first orientation;

FIG. 4 is a partial cross-sectional view of the embodiment of FIG. 3 in a use environment;

FIG. 8 is an exploded perspective view of an embodiment of the present invention;

FIG. 9 is a partial perspective view of the embodiment of FIG. 8;

FIG. 10 is a cross-sectional view taken along line 10-10 of FIG. 8;

FIG. 11 is a cross-sectional view taken along line 11-11 of FIG. 1;

FIG. 16 is an assembled view of the embodiment of FIG. 12 in a second orientation;

FIG. 17 is a cross-sectional view taken along line 17-17 of FIG. 16, placed in a use environment.

DESCRIPTION OF EMBODIMENTS

Figure 6:
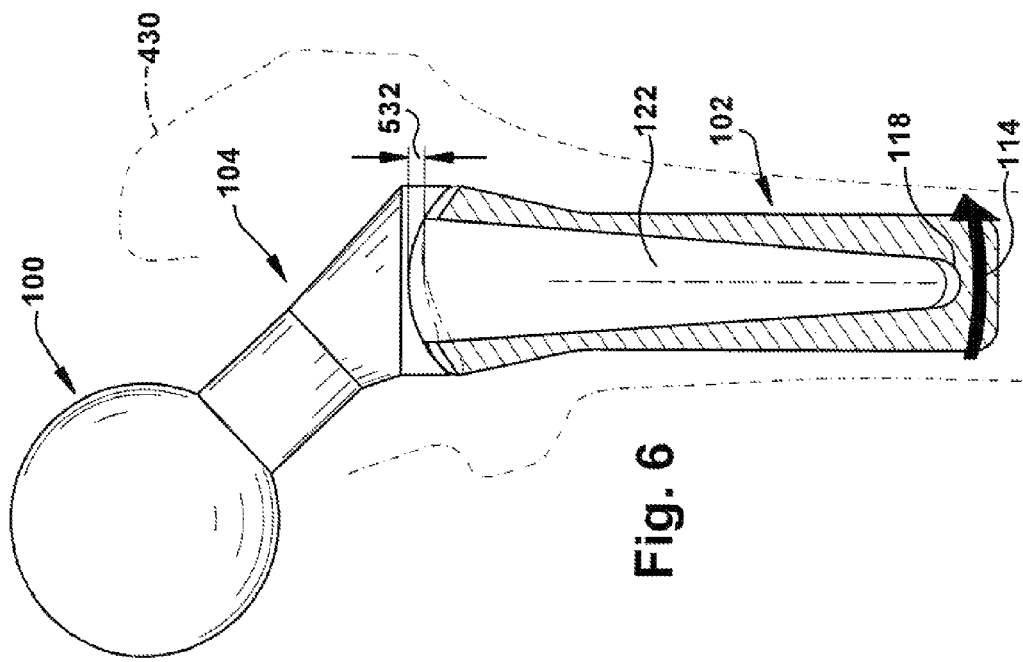
FIG. 6 is a partial cross-sectional view of the embodiment of FIG. 5 in a use environment.

In accordance with a first embodiment of the present invention, FIG. 1 depicts a multi-piece prosthetic joint component 100 including an elongate, longitudinally oriented outer sleeve 102 and a joint articulating member 104. The outer sleeve 102 includes an outer sleeve surface 106 adapted for contact with a native bone. The outer sleeve surface 106 defines a radially oriented proximal sleeve border 108 with a radially oriented proximal sleeve rim 110 intersecting the outer sleeve surface 106 at the proximal sleeve border 108. The radial orientation is defined herein with respect to the longitudinal axis 112, and may be demonstrated, for example, as being an orientation similar to that of radial arrow 114. An outer sleeve body 116 is enclosed by the outer sleeve surface 106 and the proximal sleeve rim 110. An elongate, longitudinally oriented stem-receiving cavity 118 is formed in the outer sleeve body and intersects the proximal sleeve rim 110 to define a stem-receiving aperture 120.

The joint articulating member 104 includes an elongate, longitudinally oriented stem 122, and articulating surface 124, and an interface rim 126. The stem 122 is longitudinally spaced from the articulating surface 124 and is configured for selective insertion into the stem-receiving cavity 118. The interface rim 126 is located on the joint articulating member 104 intermediate the stem 122 and the articulating surface 124.

The articulating surface 124 is shown as a spherical structure for use in a ball-and-socket joint; for example, in a traditional or inverted hip or shoulder prosthesis. However, the articulating surface 124 may have any suitable shape, size, orientation, configuration, or other property and may form a portion of at least one of a prosthetic hip joint, a prosthetic shoulder joint, a prosthetic ankle joint, a prosthetic knee joint, a prosthetic elbow joint, a prosthetic wrist joint, a prosthetic finger joint, a prosthetic toe joint, and a prosthetic spine component. For example, and depending upon the use environment, the articulating surface may be at least one of convex and concave. All or only a portion of the articulating surface 124, such as a segment of the spherical articulating surface of the Figures, might be used to contact other prosthesis components in a particular application of the present invention.

The joint articulating member 104 is shown from a different angle in the perspective view of FIG. 2. In this Figure, the joint articulating member 104 is angled to show the manner in which the stem 122 protrudes from the interface rim 126. The joint articulating member 104 used as an example herein includes a spherical articulating surface 124 longitudinally and laterally spaced from the stem 122 at a predetermined angle by a neck 228, with the interface rim 126 facing distally from a distal end of the neck.

As depicted in FIGS. 1 and 2, the proximal sleeve rim 110 and the interface rim 126 are each curvilinear in profile. The term "profile" is used herein to indicate an outline seen or represented in sharp relief or a contour, specifically when viewed in a direction perpendicular to the longitudinal axis 112. For example, at least one of the proximal sleeve rim 110 and the interface rim 126 may have a hyperbolic paraboloid, or any other desired curvilinear, profile. While the profiles of the proximal sleeve rim 110 and the interface rim 126 may be mirror-image, overlapping, or mating copies of each other as depicted here, it is contemplated that the profiles of the proximal sleeve rim and the interface rim may have relative shapes other than the negative/positive profiles shown. For example, one of the proximal sleeve rim 110 and the interface rim 126 may be curved more steeply than the other. It is also contemplated that at least one of the proximal sleeve rim 110 and the interface rim 126 may be only partially curvilinear in profile. Regardless of the specific profile of each, however, one of the proximal sleeve rim 110 and the interface rim 126 (here, the interface rim) may be substantially concave and the other of the proximal sleeve rim and the interface rim (here, the proximal sleeve rim) may be substantially convex. One of ordinary skill in the art can readily provide profiles for the proximal sleeve rim 110 and the interface rim 126 which result in a desired behaviour of the multi-piece prosthetic joint component 100.

When the stem 122 is at least partially inserted into the stem-receiving cavity 118, the proximal sleeve rim 110 and the interface rim 126 selectively interact to change a longitudinal relationship between the outer sleeve 102 and the joint articulating member 104 responsive to relative radially-oriented rotation between the stem 122 and the stem-receiving cavity 118. FIGS. 3-7C depict this interoperation of the components of the multi-piece prosthetic joint component 100.

FIG. 3 depicts the multi-piece prosthetic joint component 100 in a first, or initial, orientation. At least a portion of the stem 122 has been inserted into the stem-receiving cavity 118; in the depicted initial orientation, the stem has been fully inserted through the stem-receiving aperture 120 into a position within the stem-receiving cavity and the proximal sleeve rim 110 is in fully matched or mated contact with the interface rim 126.

FIG. 4 is a partial cutaway view with the multi-piece prosthetic joint component 100 of FIG. 3 depicted in an installed position within a native bone, shown in dashed line at 430, of the patient. Because the depicted multi-piece prosthetic joint component 100 of FIG. 4 is an elongate-stemmed component of a ball-and-socket joint, the bone 430 is shown as a femur in this example embodiment. One of ordinary skill in the art can readily provide a multi-piece prosthetic joint component 100 for a particular application of the present invention, however, regardless of the prosthesis location.

In FIG. 4, the outer sleeve 102 has been affixed into a native bone 430, such as, but not limited to, the native femur bone shown and described herein. This can be accomplished in any suitable manner. For example, the outer sleeve 102 can be affixed within an existing or created void in the bone 430 via any one or combination of adhesion, cementing, bone in-growth to a porous outer sleeve surface 106, frictional engagement (possibly augmented with a fluted or splined outer sleeve surface), pinning via a through-extending rod or screw, or any other suitable attachment mechanisms or techniques. The outer sleeve 102 need not be permanently affixed into the bone 430 before complete installation of the multi-piece prosthetic joint component, particularly in the case of a lengthy attachment process such as bone in-growth.

Also in FIG. 4, as in FIG. 3, the stem 122 is located fully within the stem-receiving cavity 118, in an initial orientation with the proximal sleeve rim 110 and the interface rim 126 in full contact. In this initial orientation, the outer sleeve 102 and joint articulating member 104 are in a longitudinal relationship having a minimum separation distance. In other words, the outer sleeve 102 and joint articulating member 104 are at maximum longitudinal compactness, with zero distance between the proximal sleeve rim 110 and the interface rim 126 in the initial orientation of the embodiment shown in FIGS. 3 and 4. It is contemplated, however, that in certain embodiments (not shown), the proximal sleeve rim 110 and the interface rim 126 may have a longitudinal space therebetween in a corresponding initial orientation, with that longitudinal space being the minimum separation distance in those nondepicted embodiments. One of ordinary skill in the art can readily provide a structure or other means to separate the proximal sleeve rim 110 and the interface rim 126 in the initial orientation, when desired.

Figure 5:
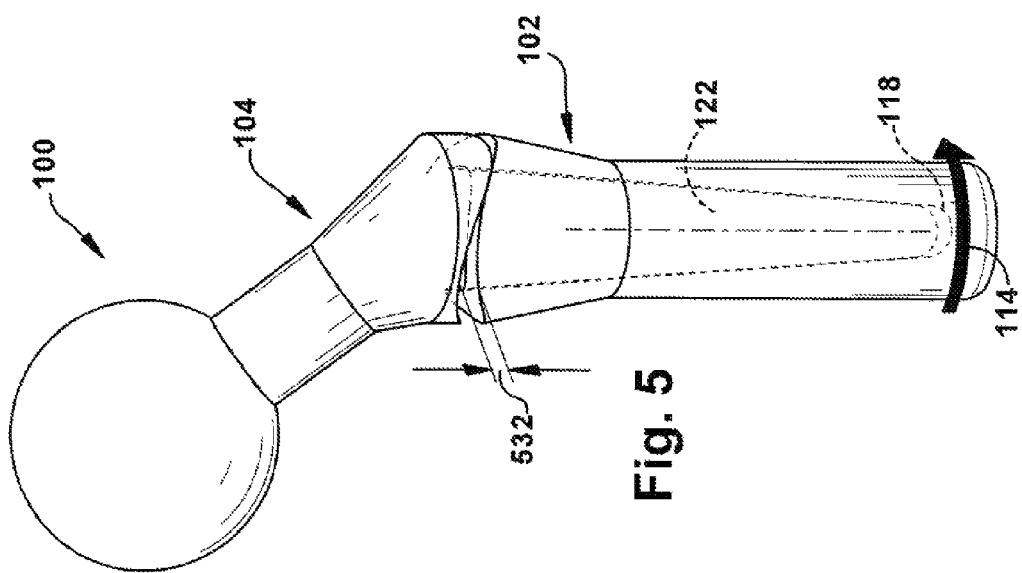
FIG. 5 is an assembled view of the embodiment of FIG. 1 in a second orientation.

Turning to FIGS. 5 and 6, the stem 122 has been rotated relative to the stem-receiving cavity 118 in a radial orientation, as indicated by radial arrow 114. This relative rotation may be caused in any manner, and by movement of either or both of the outer sleeve 102 and the joint articulating member 104 in an absolute frame of reference. For example, the articulating surface 124 may mate with a socket prosthetic member (not shown) implanted in an adjacent bone (not shown), and the joint articulating member 104 could be rotated by a force transferred from that socket prosthetic member. As another example, the bone 430 could be rotated by the patient (e.g., by swinging the leg when the multi-piece prosthetic joint component 100 is part of a prosthetic hip joint), which could rotate the outer sleeve 102 relative to the joint articulating member 104. Regardless of the way that the relative rotation is produced, the proximal sleeve rim 110 and the interface rim 126 shown in FIGS. 5 and 6 have interacted responsive to the relative rotation between the stem 122 and the stem-receiving cavity 118 to change the longitudinal relationship therebetween and accordingly provide longitudinal variance to the multi-piece prosthetic joint component.

As shown in FIGS. 5 and 6, a separation distance 532 has been created between the proximal sleeve rim 110 and the interface rim 126. The separation distance 532 represents a longitudinal expansion of the multi-piece prosthetic joint component resulting from interference between the proximal sleeve rim 110 and the interface rim 126. In other words, one of the proximal sleeve rim 110 and the interface rim 126 "rides up" on the other to push the outer sleeve 102 and joint articulating member 104 apart as a result of the curvature of the proximal sleeve rim and/or the interface rim.

As can be seen in FIG. 5, the proximal sleeve rim 110 and the interface rim 126 are not at a maximum separation distance; further relative rotation of the stem 122 and the stem-receiving cavity 118 would be needed to bring a paragee of one of the proximal sleeve rim and the interface rim to an apogee of the other, and FIG. 5 therefore shows an intermediate stage, or intermediate orientation, in the longitudinal expansion of the multi-piece prosthetic joint component 100. However, when the stem 122 and stem-receiving cavity 118 are rotated to a final orientation (not shown), the separation distance will be at a maximum, with the multi-piece prosthetic joint component 100 accordingly reaching a maximum longitudinal dimension in that final orientation.

Figure 7A:
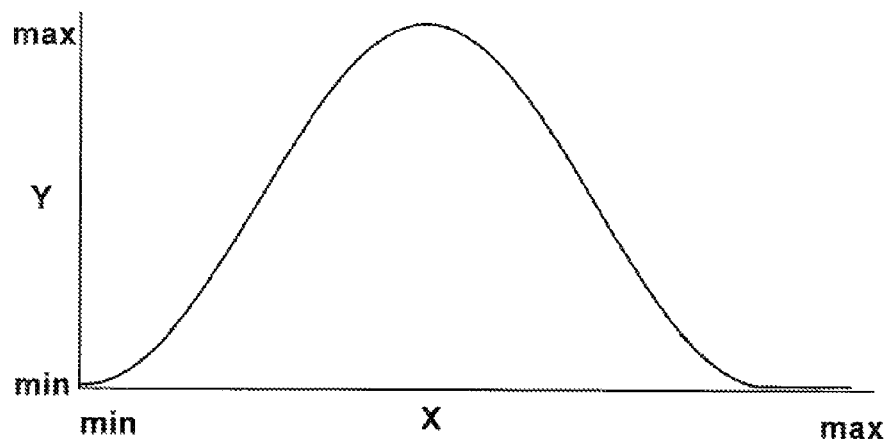
FIGS. 7A, 7B, and 7C depict example rotation-separation charts for various embodiments of the present invention.
Figure 7B:
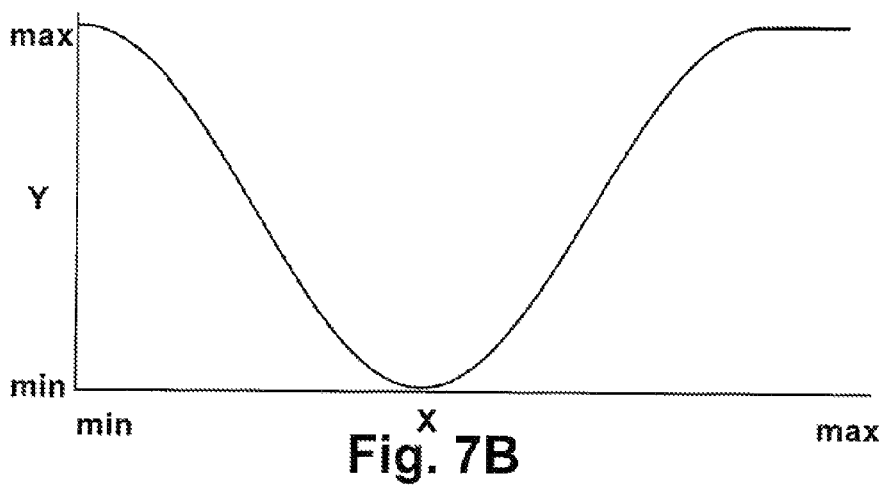
Figure 7C:
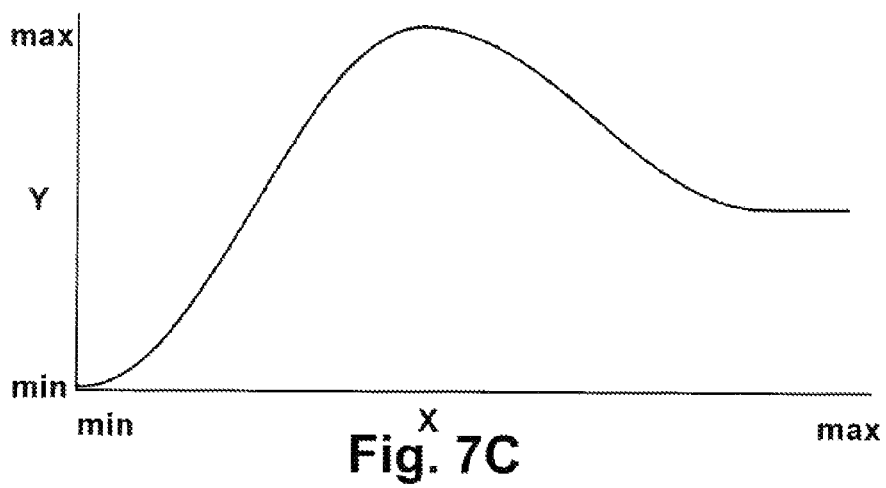

FIGS. 7A-7C schematically depict example rotation-separation charts for various embodiments of the present invention. In FIGS. 7A-7C, the profiles of the proximal sleeve rim 110 and the interface rim 126, along with the relationships of the various components of the multi-piece prosthetic joint components, have been tuned to produce desired relationships of relative rotation (rotational positioning is represented by the X-axis, with an initial or "rest" position at the origin O) to longitudinal expansion (separation distance is represented by the Y-axis). It should be noted that the min-max rotational travel shown along the X-axis may not correspond to a full 360° rotation, due to the possible presence of "stop" or limiting mechanisms or structures (not shown).

In the chart of FIG. 7A, the initial orientation is a first initial orientation (where the separation distance is at a minimum), and the multi-piece prosthetic joint component 100 includes a second initial orientation (where the separation distance is also at a minimum). The final orientation (where the separation distance is at a maximum) of the multi-piece prosthetic joint component graphed in FIG. 7A is interposed between the first and second initial orientations. Accordingly, in the embodiment graphically depicted in FIG. 7A, the stem and stem-receiving cavity relatively rotate through the final orientation during a rotation path between the first and second initial orientations.

An inversion of the FIG. 7A arrangement is shown in the graph of FIG. 7B, wherein the stem and stem-receiving cavity relatively rotate through an initial orientation during a rotation path from a first final orientation position to a second final orientation position.

In the chart of FIG. 7C, the longitudinal relationship between the outer sleeve and the joint articulating member has a secondary separation distance with the stem and the stem-receiving cavity in a secondary orientation. The final orientation (where the separation distance is at a maximum) is interposed between the initial orientation (where the separation distance is at a minimum) and the secondary orientation (where the separation distance is the secondary separation distance) such that the stem and stem-receiving cavity relatively rotate through the final orientation during a rotation path between the initial and secondary orientations. One of ordinary skill in the art can readily design a multi-piece prosthetic joint component which will have the response curve shown in any of FIGS. 7A-7C, or any other desired response curve.

Regardless of the response curve of a particular embodiment of the multi-piece prosthetic joint component, the stem 122 and the stem-receiving cavity 118 may rotate freely between the initial and final relationships. Alternately, relative rotation between the stem 122 and the stem-receiving cavity 118 could be controlled between the initial and final relationships by at least one rotation detent structure (not shown), such as, but not limited to, a series of notches or depressions in one or both of the proximal sleeve rim 110 and the interface rim 126, a ratchet mechanism, a spring mechanism, or any other suitable retarding structure or mechanism.

It is contemplated that the longitudinal relationship between the outer sleeve 102 and the joint articulating member 104 (i.e., the amount of longitudinal expansion of the multi-piece prosthetic joint component 100) could be controlled selectively between the minimum and maximum separation distances by at least one longitudinal variance controlling structure (not shown), such as, but not limited to, a constraining member preventing loss of contact between the proximal sleeve rim 110 and the interface rim 126, a friction-controlled or friction-reduced surface on one or more of the proximal sleeve rim and the interface rim, a control sleeve (not shown) surrounding the interface between the outer sleeve and the joint articulating member, or any other suitable constraining structure or mechanism. For example, the longitudinal relationship between the outer sleeve 102 and the joint articulating member 104 could be controlled selectively between the minimum and maximum separation distances by controlling an extent to which the stem 122 is inserted into the stem-receiving cavity 118, perhaps by, e.g., a filler material (not shown) placed into the stem-receiving cavity 118 before insertion of the stem 122, or in any other suitable manner.

Additionally or alternatively, a rate of relative rotation between the outer sleeve 102 and the joint articulating member 104 could be adjusted and/or controlled through the structure of the proximal sleeve rim 110 and the interface rim 126. For example, the curves of the proximal sleeve rim 110 and/or the interface rim 126 could be chosen to provide a geometry which varies the amount of force needed to provide the described longitudinal expansion in a linear or nonlinear manner as the amount of relative rotation between the outer sleeve 102 and the joint articulating member 104 changes (e.g., as the outer sleeve 102 and the joint articulating member 104 approach the end of an available relative rotation distance, more force could be required to produce the same amount of rotational motion than for rotation near the start of the available relative rotation distance).

FIGS. 8-10 depict a multi-piece prosthetic joint component 100' according to a second embodiment of the present invention. The multi-piece prosthetic joint component 100' of FIGS. 8-10 is similar to the multi-piece prosthetic joint component 100 of FIGS. 1-6 and therefore, structures of FIGS. 8-10 that are the same as or similar to those described with reference to FIGS. 1-6 have the same reference numbers with the addition of a "prime" mark. Description of common elements and operation similar to those in the previously described first embodiment will not be repeated with respect to the second embodiment.

The multi-piece prosthetic joint component 100' of FIGS. 8-10 differs from that of the first embodiment in the cross-sectional shape of the proximal sleeve rim 110' and the interface rim 126'. As shown in the cross-sectional view of FIG. 10, the proximal sleeve rim 110' has an oval profile or contour. In contrast, and as shown in the FIG. 11 cross-sectional view, the proximal sleeve rim 110 of the first embodiment has a profile which is a more regular circular shape, though need not be a perfect circle. The oval profile of the second embodiment in FIGS. 8-10 may be preferable for some patients over the circular profile of the first embodiment, and one of ordinary skill in the art can readily choose a multi-piece prosthetic joint component 100, 110' having either of these profiles, or can provide a multi-piece prosthetic joint component (not shown) having any desired rectilinear, curvilinear, combination, or any other desired profile for a particular use environment of the present invention.

FIGS. 12-17 depict a multi-piece prosthetic joint component 100" according to a third embodiment of the present invention. The multi-piece prosthetic joint component 100" of FIGS. 12-17 is similar to the multi-piece prosthetic joint component 100 of FIGS. 1-6 and therefore, structures of FIGS. 12-17 that are the same as or similar to those described with reference to FIGS. 1-6 have the same reference numbers with the addition of a double "prime" mark. Description of common elements and operation similar to those in the previously described first and second embodiments will not be repeated with respect to the third embodiment.

Figure 12:
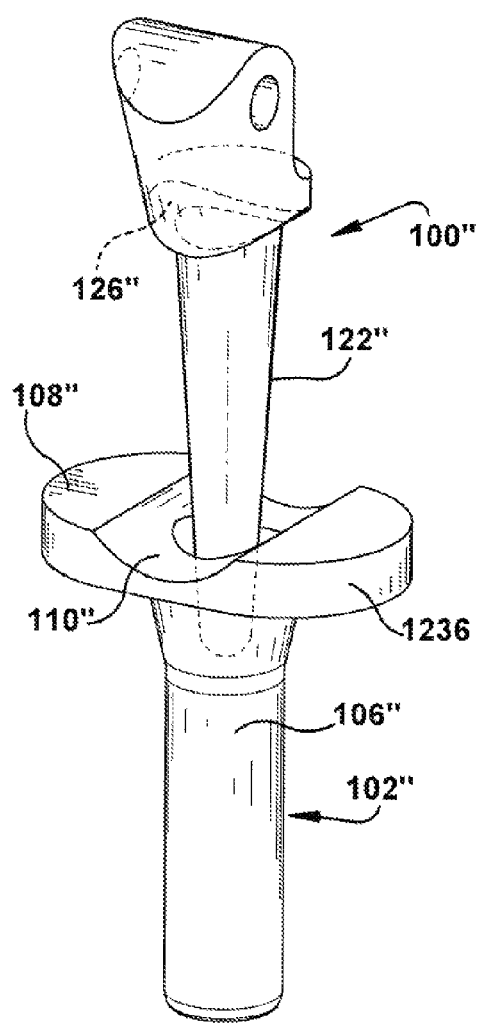
FIG. 12 is an exploded perspective view of an embodiment of the present invention.

While the multi-piece prosthetic joint components 100 and 100' of the first and second embodiments are configured for use in hip and/or shoulder joints, the multi-piece prosthetic joint component 100" of the third embodiment is configured for use in a knee joint. The multi-piece prosthetic joint component 100" shown in FIG. 12 is a tibial component comprised of an outer sleeve 102" and a stem 122". To provide context, the multi-piece prosthetic joint component 100" is shown in an initial orientation and assembled with a femoral component 1334 in FIG. 13.

Returning to FIG. 12, the outer sleeve surface 106" is markedly flared or expanded near a proximal end thereof to provide a tibial tray 1236 feature for engagement in a known manner with the patient's tibia (not shown). Therefore, the radially oriented proximal sleeve rim 110", which intersects the outer sleeve surface 106" at the proximal sleeve border 108", is only partially curvilinear in profile, at a central area thereof. However, the proximal sleeve rim 110" may have any desired shape or profile for a particular application of the present invention, and one of ordinary skill in the art can readily provide a suitable proximal sleeve rim shape. For example, and as shown, the proximal sleeve rim 110" shown in FIG. 12 is curvilinear primarily in areas which are likely to interact with the interface rim 126", which itself may have any suitable shape, as well.

Figure 13:
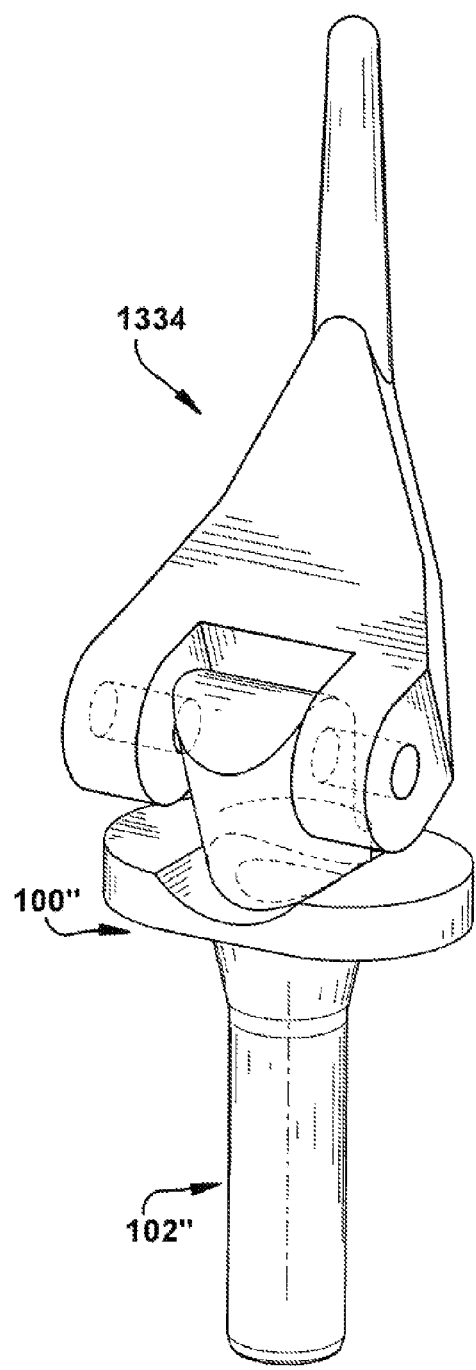
FIG. 13 is a partial perspective view of the embodiment of FIG. 12.
Figure 14:
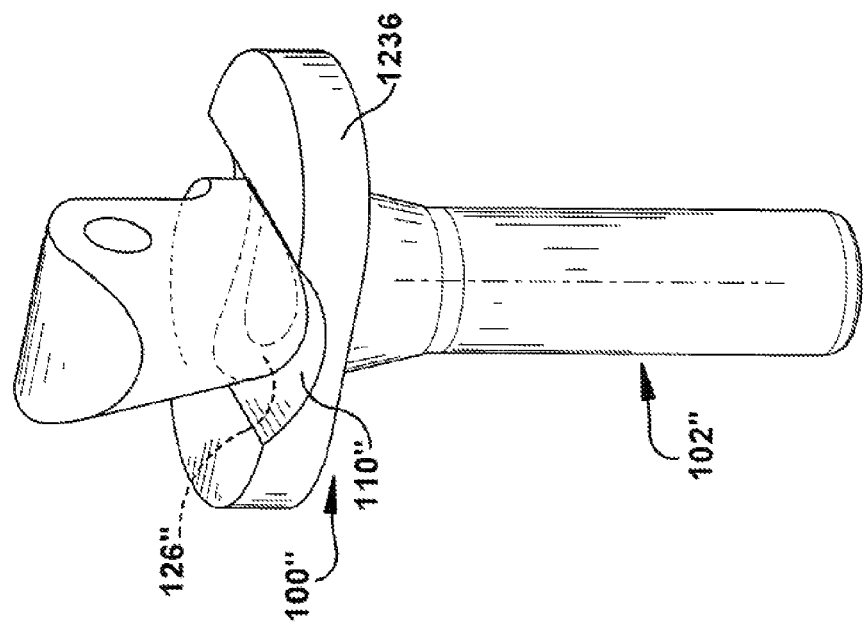
FIG. 14 is an assembled view of the embodiment of FIG. 12 in a first orientation.

In FIG. 14, as in FIG. 13, the stem 122" is located fully within the stem-receiving cavity 118", in an initial orientation with the proximal sleeve rim 110" and the interface rim 126" in full contact. In this initial orientation, the outer sleeve 102" and joint articulating member 104" are in a longitudinal relationship having a minimum separation distance.

Figure 15:
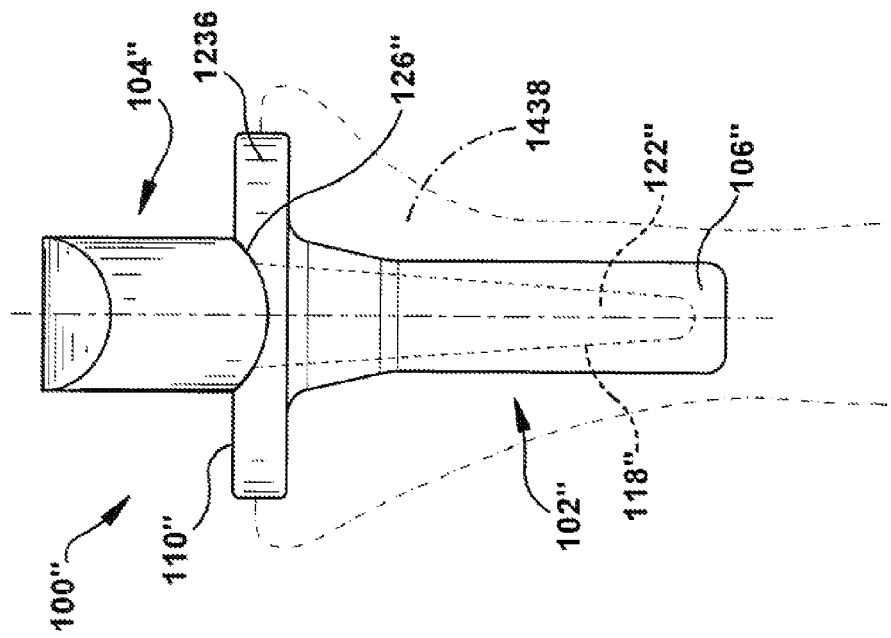
FIG. 15 is a cross-sectional view taken along line 15-15 of FIG. 14, placed in a use environment.

In FIG. 15, the outer sleeve 102" has been affixed into a native bone 1438, such as, but not limited to, the native tibia bone shown and described herein. This can be accomplished in any suitable manner.

Turning to FIGS. 16 and 17, the stem 122" has been rotated from the orientation of FIGS. 14 and 15 relative to the stem-receiving cavity 118" in a radial orientation, as indicated by radial arrow 114". This relative rotation may be caused in any manner, and by movement of either or both of the outer sleeve 102" and the joint articulating member 104" in an absolute frame of reference. Regardless of the way that the relative rotation is produced, the proximal sleeve rim 110" and the interface rim 126" shown in FIGS. 16 and 17 have interacted responsive to the relative rotation between the stem 122" and the stem-receiving cavity 118" to change the longitudinal relationship therebetween and accordingly provide longitudinal variance to the multi-piece prosthetic joint component 100". As shown in FIGS. 16 and 17, a separation distance 532" has been created between the proximal sleeve rim 110" and the interface rim 126". The separation distance 532" represents a longitudinal expansion of the multi-piece prosthetic joint component resulting from interference between the proximal sleeve rim 110" and the interface rim 126".

Figure 18:
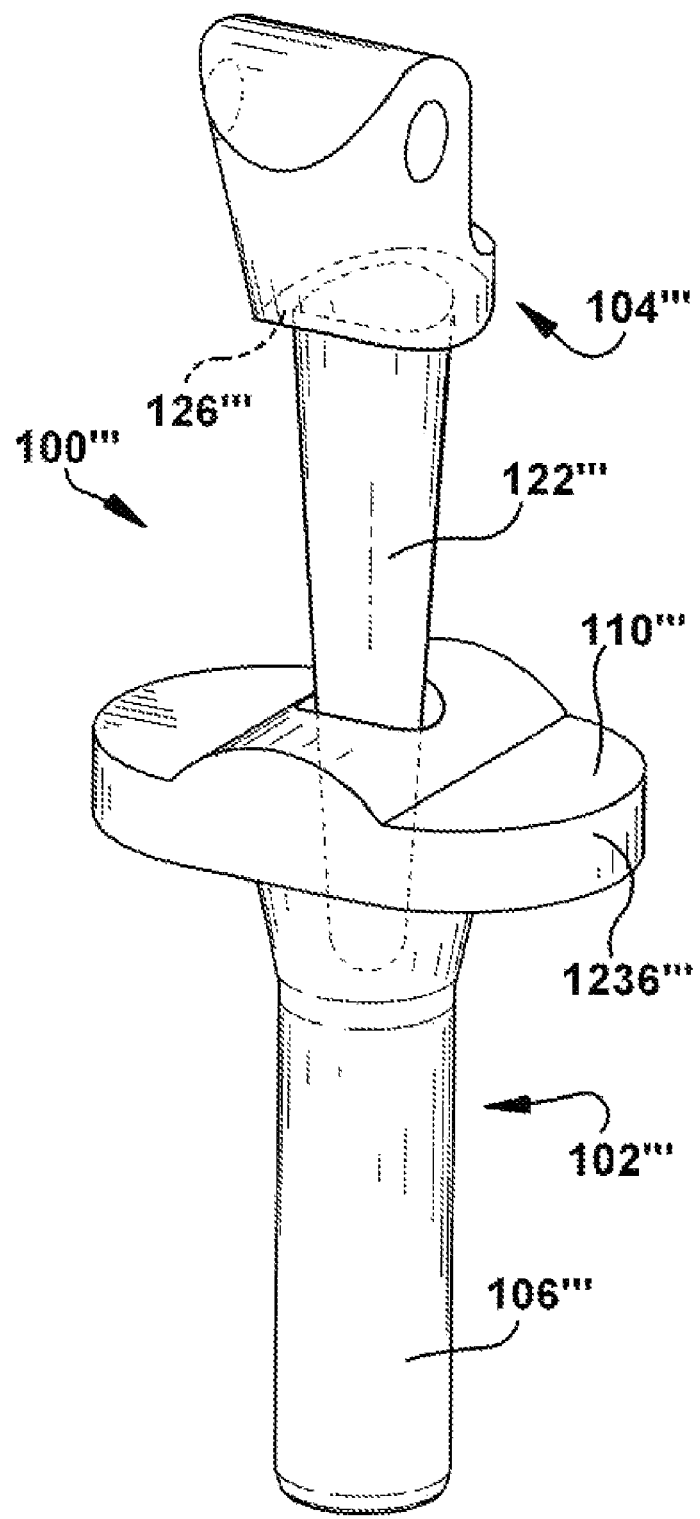
FIG. 18 is an exploded perspective view of an embodiment of the present invention.

FIG. 18 depicts a multi-piece prosthetic joint component 100''' according to a fourth embodiment of the present invention. The multi-piece prosthetic joint component 100''' of FIG. 18 is similar to the multi-piece prosthetic joint component 100" of FIGS. 12-17 and therefore, structures of FIG. 18 that are the same as or similar to those described with reference to FIGS. 12-17 have the same reference numbers with the addition of a triple "prime" mark. Description of common elements and operation similar to those in the previously described first, second, and third embodiments will not be repeated with respect to the fourth embodiment.

As shown in FIG. 18, the multi-piece prosthetic joint component 100''' is similar to that of the third embodiment. However, in the fourth embodiment of FIG. 18, the convexity/concavity of the proximal sleeve rim 110''' and interface rim 126''' are reversed from those shown in the third embodiment of FIGS. 12-17, which may be desirable for a particular application of the present invention. The multi-piece prosthetic joint components 100 and 100" of the first and second embodiments, described above, could likewise have reversed convexities/concavities from those shown.

While aspects of the present invention have been particularly shown and described with reference to the preferred embodiment above, it will be understood by those of ordinary skill in the art that various additional embodiments may be contemplated without departing from the spirit and scope of the present invention. For example, any of the structures discussed could be manufactured from component parts or integrally formed. The specific method described above for installing the multi-piece prosthetic joint component 100 is merely illustrative; one of ordinary skill in the art could readily determine any number of tools, sequences of steps, or other means/options for placing the apparatus, or components thereof, into positions substantively similar to those shown and described herein. Any of the described structures and components could be integrally formed or separately provided of any suitable material or combinations of materials; however, the chosen material(s) should be biocompatible for most applications of the present invention. Though certain components described herein are shown as having specific geometric shapes (e.g., the spherical articulating surface 124 or the converging-diverging outer sleeve surface 106), all structures of the present invention may have any suitable shapes, sizes, configurations, relative relationships, cross-sectional areas, or any other physical characteristics as desirable for a particular application of the present invention. A description of a "radial" direction or orientation with reference to a curvilinear structure should be interpreted as meaning an analogous feature or direction for a structure which includes non-curvilinear portions. A plurality of expandable joints such as that formed by the proximal sleeve rim 110 and the interface rim 126 may be located at various locations on a single multi-piece prosthetic joint component 100. Neither the proximal sleeve rim 110 nor the interface rim 126, nor any other component or structure of the multi-piece prosthetic joint component, is necessarily symmetrical across any particular plane, even if depicted as such herein. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A multi-piece prosthetic joint component, comprising:
    an elongate, longitudinally oriented outer sleeve including an outer sleeve surface adapted for contact with native bone and defining a radially oriented proximal sleeve border, a radially oriented proximal sleeve rim intersecting the outer sleeve surface at the proximal sleeve border, an outer sleeve body enclosed by the outer sleeve surface and the proximal sleeve rim, and an elongate, longitudinally oriented stem-receiving cavity formed in the outer sleeve body and intersecting the proximal sleeve rim to define a stem-receiving aperture; and
    a joint articulating member including an elongate, longitudinally oriented stem, an articulating surface, and an interface rim, the stem being longitudinally spaced from the articulating surface and configured for selective insertion into the stem-receiving cavity, and the interface rim being located on the joint articulating member intermediate the stem and the articulating surface; wherein
    when the stem is at least partially inserted into the stem-receiving cavity, the proximal sleeve rim and the interface rim interact to change a longitudinal relationship between the outer sleeve and the joint articulating member responsive to relative radially-oriented rotation between the stem and the stem-receiving cavity.

2. The multi-piece prosthetic joint component of claim 1, wherein the proximal sleeve rim and the interface rim are each at least partially curvilinear in profile, with the curvilinear portion of one of the proximal sleeve rim and the interface rim being substantially concave and the curvilinear portion of the other of the proximal sleeve rim and the interface rim being substantially convex.

3. The multi-piece prosthetic joint component of claim 2, wherein the curvilinear portion of at least one of the proximal sleeve rim and the interface rim has a hyperbolic paraboloid profile.

4. The multi-piece prosthetic joint component of claim 1, wherein the articulating surface is at least one of convex and concave.

5. The multi-piece prosthetic joint component of claim 4, wherein the articulating surface forms a portion of at least one of a prosthetic hip joint, a prosthetic shoulder joint, a prosthetic ankle joint, a prosthetic knee joint, a prosthetic elbow joint, a prosthetic wrist joint, a prosthetic finger joint, a prosthetic toe joint, and a prosthetic spine component.

6. The multi-piece prosthetic joint component of claim 1, wherein the longitudinal relationship between the outer sleeve and the joint articulating member has a minimum separation distance with the stem and the stem-receiving cavity in an initial orientation and has a maximum separation distance with the stem and the stem-receiving cavity rotated to a final orientation.

7. The multi-piece prosthetic joint component of claim 6, wherein the initial orientation is a first initial orientation, and including a second initial orientation, the final orientation being interposed between the first and second initial orientations such that the stem and stem-receiving cavity relatively rotate through the final orientation during a rotation path between the first and second initial orientations.

8. The multi-piece prosthetic joint component of claim 6, wherein the longitudinal relationship between the outer sleeve and the joint articulating member has a secondary separation distance with the stem and the stem-receiving cavity in a secondary orientation, and the final orientation is interposed between the initial orientation and the secondary orientation such that the stem and stem-receiving cavity relatively rotate through the final orientation during a rotation path between the initial and secondary orientations.

9. The multi-piece prosthetic joint component of claim 6, wherein the stem and the stem-receiving cavity rotate freely between the initial and final relationships.

10. The multi-piece prosthetic joint component of claim 6, wherein relative rotation of the stem and the stem-receiving cavity is controlled between the initial and final relationships by at least one rotation detent structure.

11. The multi-piece prosthetic joint component of claim 6, wherein the longitudinal relationship between the outer sleeve and the joint articulating member is controlled selectively between the minimum and maximum separation distances by at least one longitudinal variance controlling structure.

12. The multi-piece prosthetic component of claim 1, wherein at least one longitudinal variance controlling structure controls an extent to which the stem is inserted into the stem-receiving cavity.

13. A method of providing longitudinal variance to a multi-piece prosthetic joint component, the method comprising the steps of:
    providing an elongate, longitudinally oriented outer sleeve including an outer sleeve surface adapted for contact with native bone and defining a radially oriented proximal sleeve border, a radially oriented proximal sleeve rim intersecting the outer sleeve surface at the proximal sleeve border, an outer sleeve body enclosed by the outer sleeve surface and the proximal sleeve rim, and an elongate, longitudinally oriented stem-receiving cavity formed in the outer sleeve body and intersecting the proximal sleeve rim to define a stem-receiving aperture;

providing a joint articulating member including an elongate, longitudinally oriented stem, an articulating surface, and an interface rim, the stem being longitudinally spaced from the articulating surface and configured for selective insertion into the stem-receiving cavity, and the interface rim being located on the joint articulating member intermediate the stem and the articulating surface;

inserting at least a portion of the stem into the stem-receiving cavity;

relatively rotating the stem and the stem-receiving cavity in a radial orientation; and interacting the proximal sleeve rim and the interface rim responsive to the relative rotation between the stem and the stem-receiving cavity to change the longitudinal relationship therebetween and accordingly provide longitudinal variance to the multi-piece prosthetic joint component.

14. The method of claim 13, wherein the proximal sleeve rim and the interface rim are each at least partially curvilinear in profile, with the curvilinear portion of one of the proximal sleeve rim and the interface rim being substantially concave and the curvilinear portion of the other of the proximal sleeve rim and the interface rim being substantially convex.

15. The method of claim 14, wherein at least one of the proximal sleeve rim and the interface rim has a hyperbolic paraboloid profile.

16. The method of claim 13, wherein the articulating surface is at least one of convex and concave.

17. The method of claim 13, wherein the step of interacting the proximal sleeve rim and the interface rim responsive to the relative rotation between the stem and the stem-receiving cavity to change the longitudinal relationship therebetween and accordingly provide longitudinal variance to the multi-piece prosthetic joint component includes the steps of:

placing the proximal sleeve rim and the interface rim in an initial relationship wherein the longitudinal variance is at a minimum separation distance; and placing the proximal sleeve rim and the interface rim in a final relationship wherein the longitudinal variance is at a maximum separation distance.

18. The method of claim 13, including the step of controlling relative rotation between the stem and the stem-receiving cavity using at least one rotation detent structure.

19. The method of claim 13, including the step of selectively controlling the longitudinal variance between the outer sleeve and the joint articulating member between the minimum and maximum separation distances using at least one longitudinal variance controlling structure.

20. The method of claim 19, wherein the longitudinal variance controlling structure controls at least one of a rotational relationship between the proximal sleeve rim and the interface rim by controlling a longitudinal relationship between the stem and the stem-receiving cavity.

* * * * *